United States Patent
Beck

(10) Patent No.: US 8,041,749 B2
(45) Date of Patent: Oct. 18, 2011

(54) SYSTEMS AND METHODS OF MANAGING SPECIFICATION, ENFORCEMENT, OR AUDITING OF ELECTRONIC HEALTH INFORMATION ACCESS OR USE

(75) Inventor: Michael E. Beck, New York, NY (US)

(73) Assignee: Medox Exchange, Inc., New York, NY (US)

( * ) Notice: Subject to any disclaimer, the term of this patent is extended or adjusted under 35 U.S.C. 154(b) by 226 days.

(21) Appl. No.: 11/786,482

(22) Filed: Apr. 11, 2007

(65) Prior Publication Data

US 2007/0282843 A1    Dec. 6, 2007

Related U.S. Application Data

(60) Provisional application No. 60/791,289, filed on Apr. 11, 2006.

(51) Int. Cl.
*G06F 7/00* (2006.01)
*G06F 17/30* (2006.01)

(52) U.S. Cl. ........ 707/803; 707/610; 707/640; 707/661; 707/706; 707/713; 707/722; 707/736; 707/758; 707/791; 707/802; 707/809; 707/812; 713/173; 713/175; 713/165; 713/167; 713/166; 705/1; 705/3; 726/27; 726/28; 726/29; 726/30

(58) Field of Classification Search ............... 707/9, 10, 707/610, 640, 661, 706, 713, 722, 736, 758, 707/791, 802, 803, 809, 812, 999.1, 999.101, 707/999.102; 705/1, 3; 726/27, 28, 29, 30; 713/173, 175, 165, 167, 166

See application file for complete search history.

(56) References Cited

U.S. PATENT DOCUMENTS

| | | | |
|---|---|---|---|
| 6,516,315 B1 | 2/2003 | Gupta | |
| 7,100,206 B1 * | 8/2006 | Pere | 726/26 |
| 7,181,017 B1 * | 2/2007 | Nagel et al. | 380/282 |
| 2002/0010679 A1 * | 1/2002 | Felsher | 705/51 |
| 2003/0046564 A1 | 3/2003 | Masuda et al. | 713/193 |
| 2003/0167392 A1 | 9/2003 | Fransdonk | 713/156 |
| 2003/0216943 A1 * | 11/2003 | McPhee et al. | 705/3 |
| 2004/0122790 A1 * | 6/2004 | Walker et al. | 707/1 |
| 2005/0165627 A1 * | 7/2005 | Fotsch et al. | 705/3 |
| 2005/0197860 A1 | 9/2005 | Joffe et al. | 705/2 |
| 2006/0004588 A1 * | 1/2006 | Ananda | 705/1 |
| 2006/0010324 A1 | 1/2006 | Appenzeller et al. | 713/171 |
| 2006/0229911 A1 * | 10/2006 | Gropper et al. | 705/2 |
| 2007/0005396 A1 * | 1/2007 | Lee | 705/3 |
| 2007/0006322 A1 * | 1/2007 | Karimzadeh et al. | 726/27 |
| 2007/0143215 A1 * | 6/2007 | Willems | 705/51 |

* cited by examiner

*Primary Examiner* — Syling Yen
(74) *Attorney, Agent, or Firm* — Mintz, Levin, Cohn, Ferris, Glovsky and Popeo, P.C.

(57) ABSTRACT

Methods and apparatus, including computer program products, related to managing specification, enforcement, or auditing of electronic health information use. In general, data characterizing a request to modify access rights to health information is received and the access rights are modified in accordance with the request, where the modifying includes modifying a property characterizing access rights of a relationship between a first user and second users, or an organization of the second users. The access rights may be independent of the health information and modification of access rights may be independent of a security of the health information.

19 Claims, 5 Drawing Sheets

| FIRST PARTY | SECOND PARTY | AUTHORIZED FOR BIOGRAPHICAL INFORMATION? | AUTHORIZED FOR CLAIMS? | AUTHORIZED FOR TEST RESULTS? | TIME PERIOD |
|---|---|---|---|---|---|
| SMITH, JOHN | RESEARCH INSTITUTION FOR CANCER | NO | NO | ALL | 1/1/6-Future |
| SMITH, JOHN | LOS ANGELES HOSPITAL | VIEW | VIEW | NO | 1/1/6-Future |
| SMITH, JOHN | LOS ANGELES HOSPITAL DOCTORS | ALL | ALL | ALL | 1/1/6-Future |
| SMITH, JOHN | DOCTOR SIMPSON | VIEW, PRINT | VIEW | VIEW | 1/1/6-Future |
| CALIFORNIA INSURANCE | SMITH, JOHN | | | | 1/1/6-Future |
| CALIFORNIA INSURANCE | LOS ANGELES HOSPITAL | ALL | ALL | ALL | 1/1/6-Future |
| LOS ANGELES HOSPITAL | DOCTOR SIMPSON | ALL | ALL | ALL | 1/1/07-Future |
| BEST EMPLOYERS | SMITH, JOHN | | | | 1/1/07-Future |
| OK EMPLOYERS | SMITH, JOHN | | | | 1/1/06-1/1/07 |

FIG. 4

SYSTEMS AND METHODS OF MANAGING SPECIFICATION, ENFORCEMENT, OR AUDITING OF ELECTRONIC HEALTH INFORMATION ACCESS OR USE

CROSS REFERENCE TO RELATED APPLICATIONS

This application claims the benefit of U.S. Provisional Patent Application entitled "Trusted Third Party Authorization", filed Apr. 11, 2006, Application Ser. No. 60/791,289, the contents of which are hereby fully incorporated by reference.

BACKGROUND

The present disclosure relates to data processing by digital computer, and more particularly to managing specification, enforcement, or auditing of electronic health information access or use.

In general, health information may be managed electronically. For example, a hospital may have a database of patient information and that information may be managed through specific application software written for the hospital. Health information may refer to clinical information or administrative information regarding the delivery or receiving of care.

In addition to allowing for management of health information at a hospital, in some instances, health information may be shared outside of a hospital. For example, the MEDICAL INFORMATION BUREAU stores and shares health information among insurance companies.

Health information may be managed electronically by employers, insurance companies, government agencies, or patients using either commercially available or custom software applications, or systems that include commercially available software applications, custom software applications, or combination of both.

SUMMARY

The subject matter disclosed herein provides methods and apparatus, including computer program products, that implement techniques related to managing specification, enforcement, or auditing of electronic health information access or use.

In one aspect, data characterizing a request to modify access rights to health information is received and the access rights are modified in accordance with the request, where the modifying includes modifying a property characterizing access rights of a relationship between a first user and second users, the access rights being independent of the health information and to enable modification of access rights independent of a security of the health information.

In another related aspect, data characterizing a request to modify access rights to health information is received and the access rights are modified in accordance with the request, where the modifying includes modifying a property characterizing the access rights of a relationship between a first user and an organization comprising second users or organizations.

The subject matter may be implemented as, for example, computer program products (e.g., as source code or compiled code), computer-implemented methods, and systems.

Variations may include one or more of the following features.

Access rights may further include usage rights.

Access rights, usage rights, or both may include one or more of rights for viewing, copying, printing, or exporting health information.

Receiving requests for modification of access rights and modification of access rights may be performed, for example, by a set of services. The services may support notification of updates, access, or usage of health information. The user interface may be a website, mobile phone, or other interface.

Specifying default behaviors for authorizing users, organizations, or systems to access health information may be performed, for example, by a set of services. The specified default behaviors may be available as default settings in a user interface, such as that of a mobile phone or website, where a user may specify recipients who may require access to health information.

Health information may be stored in a computer file system, removable media, or the like. Health information may be the result of output from a computer application. Health information may be a secure electronic health record or other encrypted format. Health information may be a secure holding of a secure electronic health record. Health information need not be stored or retrieved in an unencrypted format.

Security of a secure holding may differ from security of other secure holdings of a secure electronic health record.

Access rights of a secure holding may differ from access rights of other secure holdings of a secure electronic health record.

A modified property may be stored.

A request from the second users to access or use the health information may be received at a first time later or earlier than a second time another request was received. The request may be approved or denied based on a modifying of a property of the relationship to approve or revoke access. For example, the second users may have access and usage rights to the health information, then, the access and usage rights may be revoked, such that later accesses or usages are denied to the second users.

Receiving a request to modify access rights and modifying the access rights may be performed at a server, and a client of at least one of the second users may request access to the health information. The server may determine whether to grant access depending on the property characterizing the access rights of the relationship between the first user and the second users (or, e.g., a relationship of the first user and an organization of the second users with which the second users have a relationship).

Relationships may be stored in one or more data structures including relationships of user to user relationships, organization to user relationships, user to organization relationships, and organization to organization relationships. The relationships of the data structures may be associated with one or more attributes of access and usage rights between parties of at least some of the relationships, a combination of relationships may be used to determine indirect relationships, and the relationships may describe a graph of relationships of the parties.

The subject matter described herein can be implemented to realize one or more of the following advantages. Management may be provided for control of access or usage rights for health information; tracking of accesses or uses of health information based on access or usage rights; notifications related to access or usage rights for health information; or some combination of management based on relationships of parties, such as users or organizations. For example, control of access to health information may be granted or revoked for an organization of users based on a single modification of an access rights policy associated with a relationship between the user and organization. Advantageously, a user may be notified when access or use of health information is requested such that a prompt response may be generated. For example, a patient being seen by a doctor may promptly grant access to health information or a type of health information in response to a request from the doctor. Such a workflow may remove obstacles that slow down or complicate a process of requesting access. For example, a doctor's office need not call a patient to request access, and a patient need not call an information aggregator and wait on a queue of callers to have access or usage rights changed. Access or usage rights may be modified independent of a security of health information such that, for example, access or usage rights may be granted or revoked without worrying about distribution of the health information. For example, if a hospital already has health information and a patient desires to have access of that health information revoked, the patient need not worry about the distribution of that health information at the hospital. As another example, health information may be transported to a doctor separate from requesting and receiving access to the health information, such that, for example, a large amount of health information need not be transported again. For example, a doctor may receive a compact disc full of health information from a patient and may request access to that information independent of the compact disc (e.g., through a network, such as the Internet) such that doctor need not, for example, wait for the content to be downloaded over a network connection.

Details of one or more implementations are set forth in the accompanying drawings and in the description below. Further features, aspects, and advantages will become apparent from the description, the drawings, and the claims.

BRIEF DESCRIPTION OF THE DRAWINGS

FIG. 4 is a diagram of a structure of a table of relationships and associated attributes.

Like reference numbers and designations in the various drawings indicate like elements.

DETAILED DESCRIPTION

Figure 1:
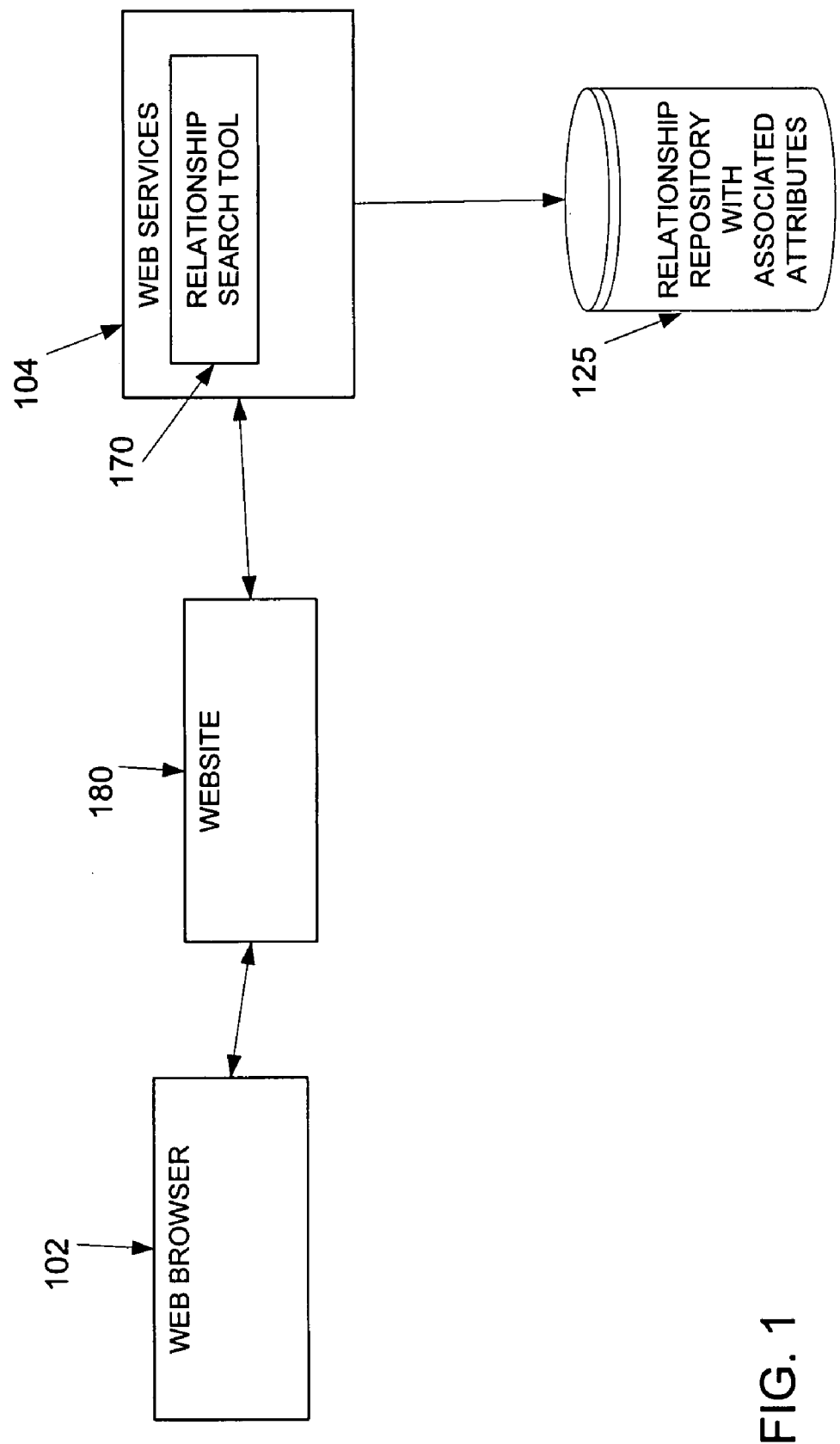
FIG. 1 is a diagram of a system for management of relationships for relationship-based health information access and usage.
Figure 2:
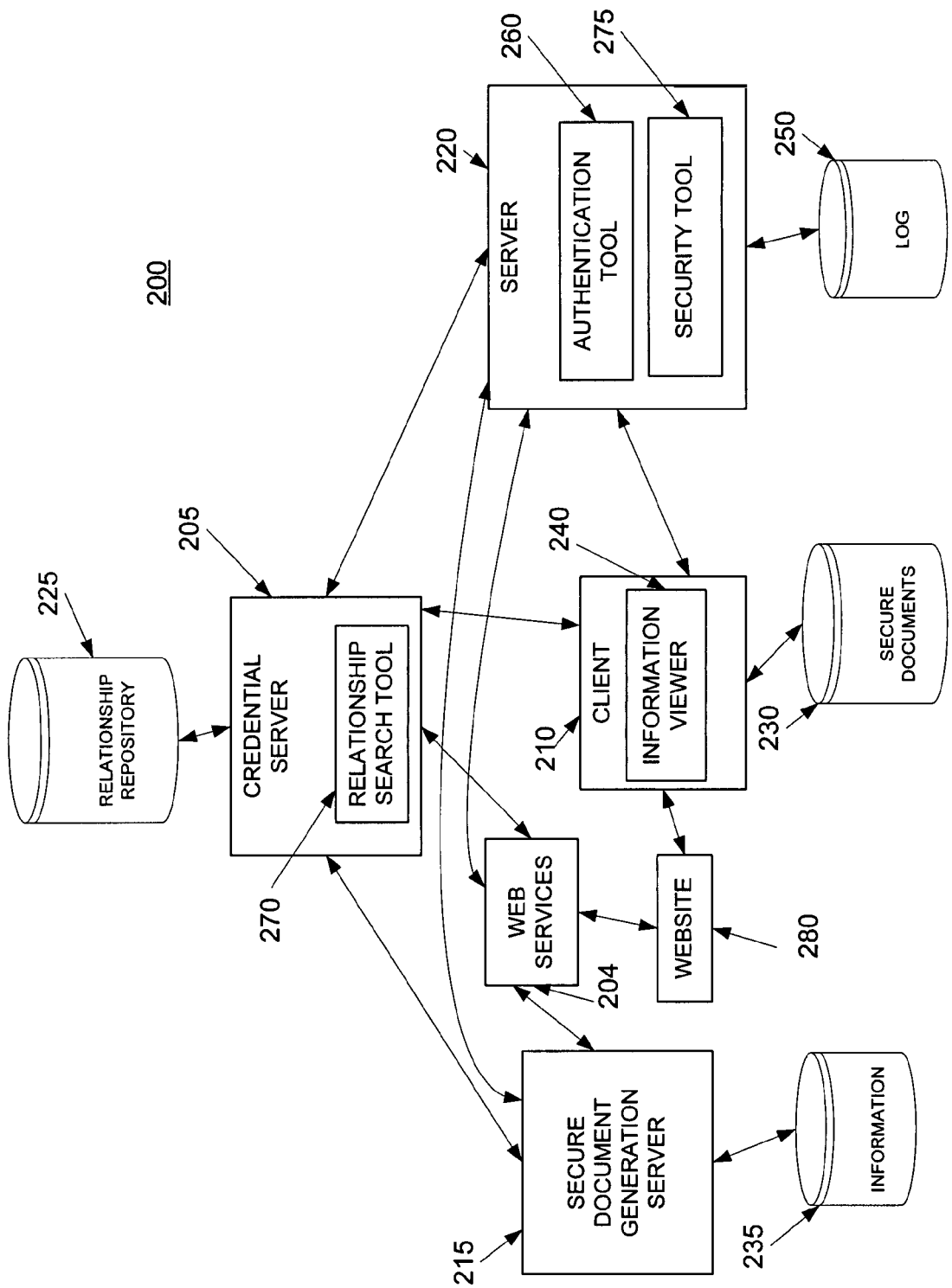
FIG. 2 is a diagram of a system to provide access and usage rights to information based on relationships.

In general, the systems 100, 200 of FIGS. 1, 2 may provide for management of control (e.g., access and usage), tracking (e.g., monitoring or auditing of access or usage), and notification (e.g., notification of access or usage, or requests for access or usage) of health information based on relationships, such as a relationship of a patient to a hospital. In the systems 100, 200, there may be a number of relevant party roles, and a user may have one or more of the roles. The roles may be implicitly or explicitly assigned. For example, a doctor requesting information about a patient may be implicitly assigned a role as a data content recipient. The roles may include: data content subject, a role describing a party about whom data is being shared (e.g. in a health information environment, it may be a patient); data content recipient, a role describing a party who is seeking access to information regarding one or more data content subjects (the data may be packaged in a 'secure container' or 'secure container holding' as will be described later); data content custodian, a role describing an owner of a source of information regarding a data content subject (e.g., in a health information environment, a doctor's office, hospital, or insurance company may have this role), which may be required by regulation or responsibility to log or control access to that information; data content publisher, a role describing an aggregator of information regarding one or more data content subjects, who may additionally be a data publisher; relationship administrator, a role describing someone who represents a governing entity responsible for maintaining, or creating data content subject, data content recipient, and data custodian accounts (e.g., in a health information environment, an employer's group benefit's administrator or an insurance company's product contract group); and, a role describing a system administrator, who at a more supreme level may manage relationships (e.g., relationships between data subjects and data content recipients) and accounts (e.g., information about a data content subject or data content custodian) in the systems 100, 200. In some implementations a program may be a user that has one or more roles. For example, a program may be a data content recipient and may request health information in the system 200 of FIG. 2.

In some implementations party roles may have variances. For example, there may be a distinction between a data content owner and data content custodian. For example, a data content subject may be a data content owner, and a data content custodian may have care over content or information of the data content owner. For example, in one system an insured party may be a data content subject and data content owner, where an insurance company of the insured party is the data content owner; however, in another system, an insured party may be a data content subject but not a data content owner, and, an insurance party may be the data content owner and data content custodian.

FIG. 1 is a diagram of a system 100 for management of relationships for relationship-based health information access and usage. The system 100 includes a web browser 102, website 180, web services 104, and a relationship repository 125 of relationships and associated attributes. In general, the web browser 102 may manage access and usage of health information from the website 180, which call the web services 104, which use the relationship repository 125 to determine a response based on the relationships and associated attributes.

In general, health information includes computer-based resources and may include data that relates to a healthcare environment, such as biographical data of a patient, and the like, and, health information may more particularly include content, such as audio, image, binary, and text files that relate to a healthcare environment. In some implementations, health information may be packaged as secure documents or components of secure documents, as discussed with reference to FIG. 2.

Management of access and usage of health information of the system 100 may be provided for the website 180 by the web services 104. In addition to management of access and usage of health information, management of tracking of access and usage, and management of notifications related to access and usage may be provided. Additional, fewer, or different services may be provided.

As an example of operation of the system 100 for managing access and usage rights associated with relationships, the relationship repository 125 may include relationships of data content subjects and data content recipients, and associated attributes describing access and usage rights of parties of the relationships. Following that example, a user of the web browser 102 being a data content subject may request to manage access and usage rights of their health information by requesting a web page from the website 180 that includes a user interface for management of access and usage rights. The website 180 may use one of the web services 104, such as the relationship search tool 170, to search for a list of relationships of the data content subject and data content recipients, and, the list may be returned as part of the website 180. The browser 102 may present the list to the user. The user may browse the list and edit relationships, including attributes of relationships. Changes to access and usage rights may be stored in the relationship repository 125 by the web services 104 and the changes may affect later requests to access or use health information, including health information that has already been distributed, such as secure documents of the secure document repository 230 of FIG. 2.

Managing of access and usage rights may include adding or removing relationships, and editing attributes of relationships such as, adding or removing access or usage rights associated with a relationship, changing conditions for access or usage rights, and the like.

Management of some relationships may be restricted to different party roles of the system 100. For example, a data content subject might be able to add a relationship such that a doctor may access or use their health information; yet, the data content subject might not be able to remove their relationship to an insurance company or employer.

Tracking of access and usage of health information may be provided by the web services 104. For example, a log, such as the log 250 of FIG. 2, may be generated for each access or usage of health information, including whether an access or use was approved or denied. The log may be viewed through the website 180 with the assistance of the web services 104. Such a log may assist with auditing of access and usage of health information.

Managing of notifications related to access and usage may be provided by the web services 104. The web services 104 may provide for notifications based on a variety of events, such as, for example, requests for access or usage of health information, events of access or usage based on a type of information or in the context of a specific relationship, updates to health information, and the like. For example, a user (e.g., a potential data content recipient) desiring to access content may send a request for access to content to a data content subject who may receive a notification indicating the requesting user desires access. Then, the user (e.g. the data content subject) may use the notification to grant access. As another example, a data content subject may request that any accesses to a certain type of health information generate a notification. As another example, a data content subject may request that any accesses of content by their insurance company generate a notification. As an additional example, a data content subject or data content recipient may request that updates to health information, such as a receipt of test results, generate a notification (e.g., a general doctor may request a notification for test results of a patient from a specialist doctor, such that the general doctor need not persistently request results).

Various types of notifications may be sent as messages, such as electronic mail messages (e.g., sent to an electronic mailing address), Short Messaging System text messages, Multimedia Messaging System text messages, messages sent within a message system for users of the website 180, and the like. The messages may be sent to a variety of destinations, such as mobile hones, personal data assistants, electronic mailing addresses, messaging systems (e.g., a messaging system of the website 180 that uses accounts, such as an account of a user for addressing a destination; or instant messaging systems), and the like.

A variety of content may be included in a notification, such as an indication of a relationship to which a notification relates, the event causing the notification, and the like.

Notifications may have access or usage rights associated with them. For example, a patient may grant access and usage rights of notifications related to their health information to a guardian or a doctor.

In general, the web browser 102 may be any type of document browser that may be used for interpreting and presenting web pages, such as web pages written in HyperText Markup Language or JAVASCRIPT.

Different types of party roles may interface through the web browser 102 to manage access and usage rights of health information. For example, in addition to data content subjects, relationship administrators may manage access and usage rights of health information. For example, a relationship administrator may add a relationship to the relationship repository 125. As another example, a data content subject may authorize the availability of allergy and emergency health information to every hospital in a twenty mile radius of their home, but require specific doctors at any of those hospitals be required explicit authorization by the data content subject to view information regarding psychiatric or substance abuse history. In managing a relationship, for example, a patient may choose to inactivate or edit or remove an established relationship in relationship repository 215 with a doctor from whom they no longer require treatment.

The website 180 may consist of one or more web pages that are static, dynamic, or a combination of the two, and the website 180 may be hosted on a web server that serves web pages and other web content in response to requests for web content.

The web services 104 are service programs that may be called by a web server using one or more communication protocols.

The web services 104 may be either stateful or stateless with respect to autonomously maintaining a conversational state through interaction with the user.

The web services 104 includes the relationship search tool 170, which may be used to assist the web service 104 in searching the relationship repository 125. In general, the web services 104 may search the relationships and associated attributes of the relationship repository 125 to respond to requests for notification, tracking, or management of control of health information, as described above. In addition, the web services 104 may alter relationships, or search for a combination of relationships to determine if two or more parties are related. For example, a combination of relationships may indicate an indirect relationship between a data content recipient and a data content subject.

The relationship repository 125 of relationships and associated attributes includes one or more data structures for storing relationships. The relationships may include user to user, organization to organization, user to organization, or organization to user relationships, but also user to system, system to system, organization to system, and the like. Additional, fewer, or different types of relationships may be included, as well. A combination of relationships specified in the relationship repository 125 may be used to infer an indirect relationship. For example, a relationship between a first user and an organization and a relationship between that organization and a second user may be used to infer an indirect relationship between the first and second users. A user, as used in reference to types of relationships, may have any of the roles described above, such as a data content subject.

The relationship repository 125 may be stored in one or more data structures, such as one or more tables. Advantageously, the use of relationships may allow for a graph-based view of parties (e.g., users and organizations). For example, a user may belong to multiple organizations by having multiple relationships where the organizations are parents. For example, a user may have multiple employers being parents in multiple relationships.

Data structures supporting storage of relationships may be one or more logical or physical tables in a, but not limited to a computer-based resource, data source, database, memory, or configuration. Data structures may be facilitated using the assistance of a combination of a directory and other mechanisms for relationship storage. Data structures, given a time-phase and source node of reference to provide context, can be used to mimic a hierarchical directory structure. Protocols available for accessing directories (e.g., Lightweight Directory Access Protocol) and applications for which directory structures are used (e.g., authentication, authorization, identity management, and the like) may be supported by the implementation of these structures.

Having multiple parents, references to other parent's child nodes, or sibling nodes may assist in having records of users that exist beyond an existence of a relationship. For example, a user may have a relationship with a past employer and a relationship with a current employer. In some contexts, such as a health care environment, having information about past and current relationships may be helpful. For example, if a user switches insurance companies past and present relationships may be used to find information about a user.

Relationship repository 125 may be implemented using a hierarchical data structure, such that it may convey the limitations of storing relationships that relationship repository 125 is intended to resolve.

Additional relationships stored in relationship repository 125 may be expressed in a second, non-hierarchical data structure, multiple non-hierarchical data structures, or multiple hierarchical data structures, or combination of any of the aforementioned techniques. Additional relationships do not need to be stored in the same relationship repository 125, in which case web services 104 may be responsible for brokering requests among multiple relationship repositories 125, aggregating responses to facilitate processing. Multiple responses may not be necessary for web services 104 to determine relationships.

Different types of attributes may be associated with a relationship. For example, in implementations involving use of relationships to determine access rights, attributes may include a time interval of a relationship, types of content authorized for a relationship, types of authorized access, and the like.

There may be different types of relationships and a type of relationship or set of relationships may be characterized as a profile, where a profile may characterize a collection relationships, or a collection of relationships and their associated attributes, a collection of relationships and their associated attributes with predefined values, or a collection of attributes, or a collection of attributes with predefined values. For example, a same combination of parties may have multiple profiles for a relationship, which may be expressed as multiple relationships each having a different set of associated attributes, a single relationship having multiple associated profiles (e.g., as attributes), or a combination of the two techniques. As another example, a profile may be a template of parameters of attributes for relationships.

Profiles may be assigned different types of attributes, including all attributes associated with a relationship. For example, in implementations involving the use of profiles to characterize relationships that may be used to determine access rights, profile attributes may include a time interval of a profile, types of content authorized for a profile, types of authorized access, and the like.

In constructing a relationship, a user may chose among pre-specified profiles to select one that is applicable to serve as the starting template for a relationship, at which point a new instance of a relationship may be generated from that profile and customizations applied may be saved to that relationship or to the profile used in that relationship's generation, or both.

Profiles may be created by explicit or implicit specification. For example, a user may create a profile type to be applied when asserting relationships with doctors, but also, a profile type may be created by the computer application for the user on the basis of how it is observed the user typically specified relationships with doctors.

Profiles may be shared among users. Profiles may be stored as a data structure, in the relationship repository 125. Profiles may be offered as features of a software program and made available to users on a basis of user demographic information, articulated relationships, or state of residence.

Profiles may be restricted for purpose of creating a relationship by the specification of one or more rules that may constrain the use of that profile. For example, it may be illegal for a patient to restrict a doctor from accessing a specific type of information if either the patient or the doctor is resident or providing or receiving care in a given jurisdiction; in this case, a profile creating such a restriction would be inapplicable to the relationship between the patient and the doctor.

Although FIG. 1 includes an interface including a web browser 102 and website 180, other types of interfaces may be used. For example, a mobile phone, interactive voice response system, or personal digital assistant may interface with the web services 104. Also, a combination of different types of interfaces may interact with the web services 104. Also, in some implementations, a program may cause interactions that interface with the web services 104 instead of a user being a person interacting through a user interface with the web services 104. For example, a program may automatically manage access rights of a data content subject with the web services 104 (e.g., as part of a business process, for example, of adding a data content subject as an insured party of an insurance company).

Although web services 104 are used as an example of tools for providing managing access and usage of health information, tracking of access and usage of health information, and notifications related to access and usage of health information, implementations may vary. For example, a set of tools may be accessible by an application programming interface and may provide same or similar operation. As another example, web services 104 may be implemented as programming interfaces (e.g., an application programming interface). For example, website 180 may communicate directly with relationship repository 125 through the programming interfaces.

Although the system 100 of FIG. 1 includes a certain combination of features, additional, different, or fewer features may be included. For example, the relationship search tool 170 need not be included and the web services 104 may perform searching of the relationship repository 130 without assistance of a tool. As another example, the relationship repository 125 may include relationships but need not include associated attributes (e.g., an existence of a relationship may imply access rights). As another example, although the web services 104 include the relationship search tool 170, such a tool need not be part of the web services 104. For example, the web services may be separate from the relationship search tool 170.

As another example, the website 180 and the web services 104 may be hosted together or separately. The web services 104 and the website 180 may be operated together or separately by a data content publisher (e.g., health information provider, insurance company, doctor's office, hospital, and the like). The web services 104 may support presentation of data to multiple websites, such as the website 180. The web services 104 may be customized for unique requirements of each website 180. Presentation of health information in website 180 may be controlled by a role independently of roles assigned the health information.

FIG. 2 is a diagram of a system 200 to provide access and usage rights to information based on relationships. The system 200 includes a client 210, a server 220, secure documents 230, a credential server 205, a relationship repository 225, a secure document generation server 215, an information repository 235, and a log repository 250. Components of the system 200 that are same or similarly named or numbered as components of the system 100 may perform same or similar operations (e.g., a repository search tool 270 of FIG. 2 may perform the same operations as the repository search tool 170 of FIG. 1).

In general, in the system 200, information from the information repository 235, such as health information, may be secured as secure information in a component of a secure document or a secure document such that the client 210 may only perform actions with the information (e.g., a component of a secure document or an entire secure document) after obtaining authorization from the server 220, where that authorization is based on relationships (e.g., an existence of a relationship or attributes of a relationship; e.g., between a data content recipient and a data content subject). From the generation of secure information to its viewing, the sequence may be as follows. Information from the information repository 235 may be packaged and secured in a document by the secure document generation server 215 in accordance with a specification for organizing the information and a policy of maintaining security (e.g., terms and conditions). A policy or policies for organizing the information and maintaining security may be determined by preferences of a data content owner or data content subject as identified by a query of the credential server 205 (e.g., based on preferences associated with a relationship of a data content subject and data content recipient).

Figure 3:
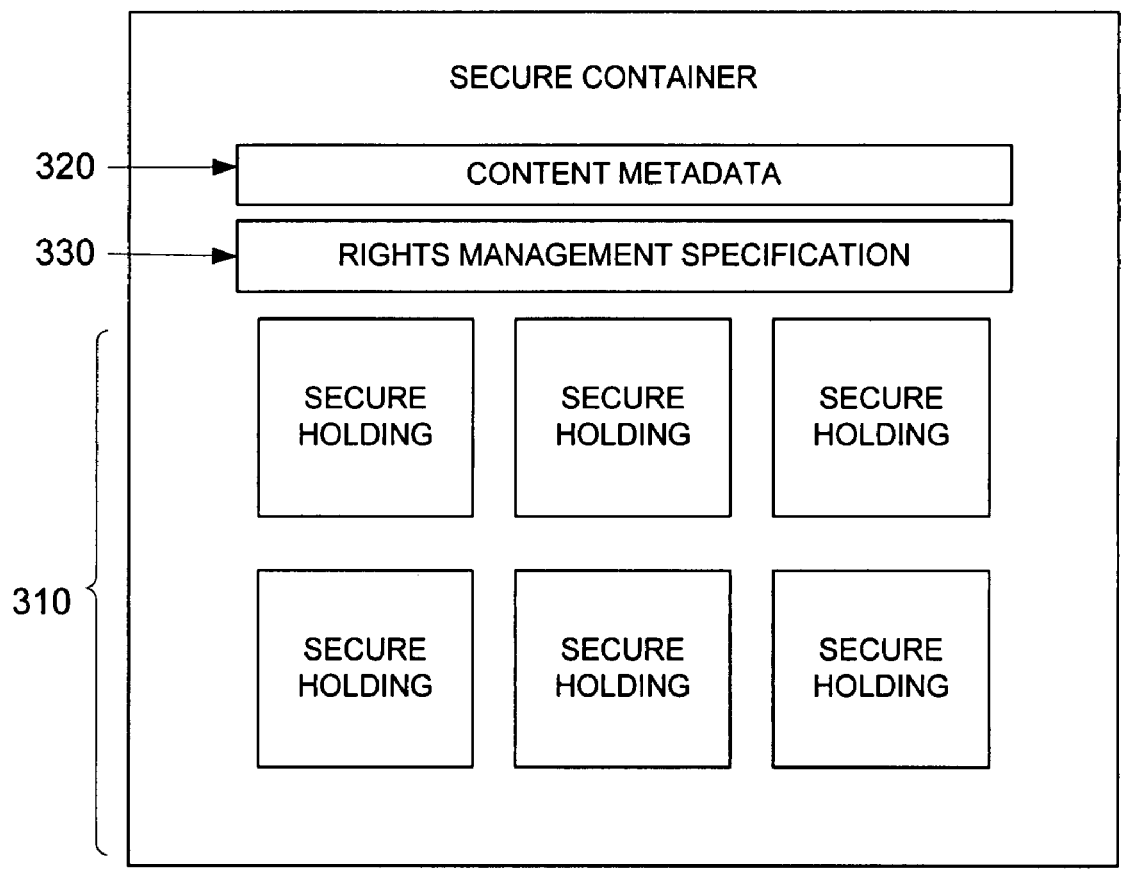
FIG. 3 is a diagram of a structure for a secure document.

In general, a secure document may be a secure container for computer-based resources, such as information or content, such as a secure container structure 300 of FIG. 3 and each of the components of a secure document may be one of secure holdings 310, which contain computer-based resources. Components of the secure documents at the repository 230 may be electronic documents or references to resources, such as electronic documents. For example, components of secure documents may include such computer-based resources, or content, as audio, image, binary, and text files; these types of content and other computer-based resources, either singularly or in the aggregate collectively also referred to as a computer files or documents. As another example, a reference to a computer-based resource, such as a uniform resource indicator (URI), may be encrypted in a component of the secure document, the component may be decrypted, and the uniform resource indicator may be used to download and access the computer-based resource referred to by the uniform resource indicator.

In general, the web services 204 perform data, process, or service-type integration with other components of applications or data sources to support features of the website 280. As examples, the web services 204 may manage control of access or use of information (e.g., with assistance of the credential server 205 and the relationship repository 225; e.g., default management settings, such as settings to provide a default mechanism to access or use information); tracking of access or use of information (e.g., with assistance of the server 220 and the log 250), and preferences for tracking (e.g., with assistance of the credential server 205 and the relationship repository 225); notifications related to access or use of information (e.g., with assistance of the server 220 and the log 250) and preferences of notifications (e.g., with assistance of the credential server 205 and the relationship repository 225); and requesting generation of secure documents from the secure document generation server 215.

The client 210 may allow for access and usage of components of secure documents of the repository 230.

The client 210 may request information from a website 280, which requests information from the secure document generation server 215 (e.g., through the web services 204). The client 210 may be authorized for downloading of information by the website 280, which receives secure documents or components of secure documents from the secure document generation server 215. In some implementations, the secure document generation server 215 need not publish back to the website 280. For example, secure documents or components of secure documents may be sent to a user in an electronic mail message, published to the repository 230 of secure documents (which, for example, may be shared by multiple clients), and the like. In some implementations, a user need not use the client 210 to request information from the website 280 (e.g., the requesting of information and its viewing need not be combined features of the client 210).

As an example of the client 210 requesting information, the website 280 may receive credentials, such as a user name and password, from the client 210. Alternatively, also as example, a user may request content directly from the website 280. In either case, if the user is authenticated and authorized, the information may be downloaded. Following the example, the website 280 may contact the secure document generation server 215 for information. The secure document generation server 215 may contact the credential server 205 with the credentials to determine whether the user of the client 210 is authenticated and whether the user is authorized to access information by checking the relationship repository 225, which may include a list of users, credentials, and information that may be used to determine whether a user is authorized to access specific information (e.g., a table of relationships between a data content recipient and a data content subject with attributes describing access rights based on the relationships). If the user is authorized, the secure document generation server 215 may receive from the credential server 205 a policy of usage of the information (e.g., terms and conditions to be packaged with the information) and policy of generating the data (e.g., specification of a format for the data; e.g., a layout or specification of filtering of data).

The information that is requested by a potential data content recipient need not have a one to one cardinality between a data content subject and a data content recipient. For example, information may be requested for a number of data content subjects by a single data content recipient. In some cases, content related to multiple data content subjects may be necessarily or, alternatively, for convenience be packaged in a single secure document. For example, panel data that may be distributed in the interest of public health may be requested and that panel data may be based on multiple data content subjects. To accommodate for multiple secure content subjects, the secure document generation server 215 may be able to generate a secure document with components that respect terms and conditions of use associated with each of the multiple data content subjects (e.g., a variety of policies may specify different terms and conditions for different data content subjects, and terms and conditions of those policies may be embedded in a secure document and adhered to by the client 210).

Policies for packaging of information may depend on a data content recipient (e.g., for a recipient of a certain insurance company in Massachusetts, insurance companies in Massachusetts may have certain requirements different from other states or that company may have preferences that differ from other companies), relationship of data content subject and data content recipient, and the like. The secure document generation server 215 may package the information in accordance with policies provided by the credential server 205. Then, the user of the client 210 may download or otherwise receive the information as part of a secure document. In some implementations, access for downloading of information may be restricted and the secure document generation server 215 may contact the credential server 205 to determine whether information may be downloaded by an authenticated user or accessed by an authenticated user of the client 210.

To view or otherwise access or use the information, the client 210 may request access or usage from the server 220 by sending credentials for the user, and the secure information as a component of a secure document or a secure document (e.g., from the repository 230). Then, the server 220 may determine the user of the client 210 is authenticated based on the credentials based on communication with the credential server 205, the server 220 may determine whether the user of the client 210 is authorized to access the information based on communication with the credential server 205, and, the server 220 may decrypt the information and send the information to the client 210. For example, the credential server 205 may use credentials to authenticate a user and relationships of the user at the relationship repository 225 may be used to determine whether the user is authorized to access the information. For example, an existence of a relationship may indicate authorization, or attributes of a relationship may indicate authorization.

Authentication of user may be a function of client 210 or a function of server 220. Authentication of user may occur each time the client 210 makes a request for access or usage from the server 220. Credentials need not be presented each time a request for content is made. For example, authentication may be provided for a duration, such as a duration of a secure server session. As another example, client 210 or server 220 may cache credentials as a component of a set of interactions with the user.

Credentials may be used to gain access to features or resources of client 210 or server 220, other than secure documents. For example, credentials may provide access to additional menu features of the client. For example, credentials may provide additional information to be generated by the server 220 to be passed back to the client. A user of client 210 may be authenticated at the client, but not authenticated at the server. A user of server 220 may be authenticated at the server, but not authenticated at the client. The credentials provided by a user to the client 210 may be communicated to the server 220, such that relationships in relationship repository 225 may provide the basis for the issuing of additional or improved credentials, or the revoking of existing credentials to the user.

The repository 230 may be shared among a number of potential recipients (e.g., a file server, and the like), shared between a number of potential recipients and data content subjects (e.g., a mobile phone, personal digital assistant, UNIVERSAL SERIAL BUS drive, and the like), or represent the attachment of the secure format to another secure or insecure format (e.g., as an email attachment, a multimedia mobile message service communication, network message, peer-to-peer computing communication, and the like).

Not all secure documents need be stored at the repository 230. For example, the repository 230 need not store all information communicated between the client 210 and server 220. For example, the server 220 may present the client with a web page that the client 210 is capable of rendering or has no use for after the initial time the information is presented by the server 220. Subsequent web pages or information can be communicated from the server 220 to the client 210. Server 220 may provide client 210 with structured or unstructured information that need not be transmitted as a web page.

If the client 210 is authorized to access or use the information, the server 220 may enable access or use at the client 210. For example, the server 220 may decrypt secure information and send the information to the client 210 in accordance with another security. Enabling access at the client 210 may include sending to the client 210 a version of a secure document having first type of security removed in lieu of a second type of security that can be removed by the client 210.

To send the information to the client 210, the server 220 may secure the information in accordance with a session key negotiated with the client 210 or using other techniques or mechanisms that enable the client 210 to access the information.

In implementations involving different types of access and usage rights, the server 220 may receive an indication of a type of access or usage requested and the server 220 may approve or deny a specific action.

Types of access and usage rights may depend on a user of the client 210 (e.g., different access and usage rights may be associated with different relationships of data content recipients and a data content subject), and the client 210 may enforce those access and usage rights and prevent unauthorized access. In some implementations, access and usage rights may be restricted based on terms and conditions of a secure document or component of secure document that are included in a secure document. Access and usage rights may also be restricted based on capabilities of the client 210 to provide security or reliably restrict access or use by a data content recipient. In addition, the terms and conditions may differ depending on a role of a data content recipient. For example, a system that accesses information as the client 210 may have a role as a research institution, and terms and conditions for usage of the information may be enforced based on that role (e.g., terms and conditions may differ across different roles). For users having multiple roles, different conflict resolution procedures may be adhered (e.g., a broadest or most restrictive set of terms and conditions may be adhered).

In some implementations, the process of the server 220 may generally be viewed as moving information from a first trusted environment (e.g., information as it is secure from the secure document generation server 215) to a second trusted environment (e.g., a secure server session) by removing a first security and adding a second security. The server 220 may also remove first security and add a second security for reasons other than changing trusted environments, including updating security with a type of security considered more secure, updating security with a type of security of varying strength or algorithm characteristic, or updating security with security supported with credentials that are issued to replace credentials that have expired with regard to previous security (e.g., a different set of credentials to be used to decrypt components of secure documents), or changing security as may be necessitated for distribution of content (e.g., for security supported by another platform).

The first security and the second security may use same or different techniques, mechanism, or a combination of the two. For example, the first security may use a same encryption technique as the second security but may require different credentials. As another example, the secure documents of the repository 230 may be encrypted using a first security technique and the security tool 275 may be used to remove the encryption. Then, the security tool 275 may use a second type of security, such as a secure server session between the client 210 and server 220 to send the secure document or part of the secure document to the client 210. Advantageously, the first security of secure documents might only be removable at the server 220 to enhance security of the secure documents and the computer-based resources they contain (e.g., to avoid having to send a cryptographic private key to the client 210 to decrypt secure documents, which might jeopardize a trusted use of that private key, should the key be intercepted or otherwise obtained by an unauthorized party).

As an example of implementations in a health care environment, electronic medical records of a data subject may be stored in an encrypted format at the repository 230 of a data recipient. The data recipient may request access from the server 220 to view a medical record through the client 210 by sending credentials, the medical record, and a requested type of access to the server 220. Based on the credentials authenticating the user of the client 210 and authorization based on a attributes associated with a relationship of the user, the server 220 may decrypt the record and re-encrypt the record in accordance with a session key negotiated with the client 210. The record, encrypted with the session key, and access rights for the record may be sent back to the client 210 by the server 220. Then, the client 110 may allow usage of the record in accordance with the requested action. Access and usage of the record may be in accordance with terms and conditions specified in the secure document, or the component of the secure document. In some implementations, components of a secure document, rather than an entire secure document, may be requested for access, sent to the server 220, and decrypted.

The client 210 may allow for different types of access of secure documents of the repository 230. The types of access may include viewing, copying (e.g., copying and pasting of text, screen captures, export of data, and the like), modifying, printing, and the like. The client 210 includes an information viewer 240. The information viewer 240 may present documents to a user for which the client 210 has access rights and allow for types of access other than viewing to be performed depending on access rights granted to the client 210. For example, a user of the client 210 may be prevented from any type of access, in which case, a document might not be viewable. As another example, a user of the client 210 may be allowed to view and print documents, but, might not be allowed to copy or modify documents.

To ensure enforcement of access and usage rights, the client 210 may be required to be a trusted client. For example, the client 210 may be authenticated by the server 220 as a client that ensures enforcement. For example, the client 210 may send authentication information to the server 220 to indicate the client 210 is a proper client for authorizing access or use of secure documents. For example, the client 210 may be proprietary to ensure enforcement of security (and, prevention of unauthorized access) or may be certified as following a specification for clients (or, client environments). For example, the client 210 may be a tool in a suite of software tools that make up an application and the tool may be certified as a client complying with a specification for security enforcement. As another example, the client 210 may be a suite of software tools or programming interfaces that ensure enforcement of access and usage rights.

Client 210 and server 220 may use a communication protocol (e.g.: HTTP) or secure communication protocol (e.g., SHTTP) to communicate. The client 210 may request access rights from the server 220 by, as examples, establishing a secure server session, sending an application to application message, and the like. The request may include different types of information. For example, a request may include metadata for a document and a secure version of the document. In addition to metadata, other information may include, as example, a version of the client 210 or a component of the secure document (e.g., requested for access), cryptographic key specifications (e.g., a reference or description of a key used for the component), or cryptography algorithms enforced or required for document security and access/use.

Advantageously, including a document as part of a request may allow for distributed storage of documents and may facilitate transport of documents, as the server 220 need not store secure documents and users need not contact the server 220 to receive documents (e.g., secure, encrypted documents may be transferred or accessed via electronic mail, a UNIVERSAL SERIAL BUS-compliant memory key, mobile phone, personal digital assistant, and the like). In addition, the document may be signed (e.g., cryptographically signed) such that the client 210 or server 220 may authenticate the document (e.g., to indicate a document has not been altered). In some implementations, to reduce network bandwidth consumption or unnecessary storage by data content recipients, secure documents or portions of secure documents may be cached or stored at the server 220 and a request from client 210 may simply identify a secure document or portion of a secure document to be accessed without including that content along with user credentials and proposed action for usage at client 210, such that the secure document or portion of secure document, which may be accessible only to server 220, may have first security removed and second security added, and secure document or portion of secure document with second security is sent back to client 210.

The information viewer 240 of the client 210 may allow for exploring of secure documents or parts of secure documents of the repository 230. For example, a user of the client 210 may browse a list of secure documents and may select a secure document to view, which may cause the information viewer 240 to request access for viewing the selected secure document. The repository 230 may be remote (i.e. not proximal) from the client 210 such that secure documents or secure document parts may be accessed by browsed using protocols including FTP (File Transfer Protocol), WebDAV (Web Distributed Authoring And Versioning), HTTP/SHTTP (HyperText Transfer Protocol/Secure HyperText Transfer Protocol), and the like. The client 210 may be embedded in other application or called by another application as a plug-in or helper to assist with the content type associated with the secure document or component of secure document type used for communication between client 210 and server 220 in a specific computing or operating environment. This association may occur by mechanisms including Internet Engineering Taskforce (IETF) specification compliant MIME (Multipurpose Internet Mail Extensions) type or operating system extension.

To allow for management of secure documents before access and usage rights have been granted, some metadata of the secure documents may be viewed. For example, a name of a computer-based resource stored as a component of a secure document or a short description of that component of a secure document might be used and need not be secured from viewing by a user who has not been authenticated or authorized.

The server 220 may authorize access and use of secure documents of the repository 230 by authenticating a user with an authentication tool 260, authorizing the user, and by removing security of a document with a security tool 275. In addition to removing security, the security tool 275 may be used to apply security to the document. For example, a user may request access to a document by sending a request from the client 210 to the server 220 and the server 220 may authenticate the user of the client 210 with the authentication tool 260. Then, if authenticated and authorized, the security tool 275 may be used to remove the security from a secure document, and, the document may be sent to the client 210 with a different, second security for the document. This second security may be specific to the client 210, the user of client 210, or negotiated as a characteristic of the specific use or request.

The packaging and securing of information by the secure document generation server 215 may occur in response to a request for information from the client 210 or in response to other stimulus. For example, in a medical environment, a doctor may request results of an exam and that information may be packaged in a particular format and secured at the secure document generation server 215. Documents may be encrypted using a cryptographic public key that corresponds to a cryptographic private key that is necessary for decryption at the server 220. In some implementations, any number or types of security may be applied at the secure document generation server 215. Different types of security may have different strengths (e.g., one cryptographic algorithm may be inherently stronger than another, or alternatively the same cryptographic algorithm may be made stronger by altering the keys or other inputs to the algorithm used). The format for generating a secure document may be the format described with reference to FIG. 3 and preferences of the format of information of the holdings may be determined with reference to policies provided by the credential server 205. In some implementations, a number of formats may be supported (e.g., for different systems that use different formats). Many different types of information may be in the information repository 235. For example, in a health care environment, the information may include insurance claims, bills, x-rays, test results, signed waivers, doctor observations, a medical history summary, and the like.

Any number of secure document generation servers may be deployed for distributed secure document generation. For example, in a health care environment, a number of secure document generation servers may be distributed across different insurance companies and hospitals for generating secure versions of their respective information.

To deal with updates to data, changes may be required to be performed at a source, such that a secure document generation server, such as the secure document generation server 215, packages and secures updated data. Once changes have been made, access to secure documents in circulation may be disabled (e.g., a request of the server 220 to view a secure document or component of the secure document may be denied) and parties seeking access to changed information may be notified that updates may be retrieved. In some implementations, status or awareness of updates may be published. For example, the secure document generation server 215 may publish updates to the client 220 or the website 280.

In general, the credential server 205 manages polices for access and usage of information, including specifications or policies of packaging of information in secure documents, such as in accordance with the structure 300 of FIG. 3, and usage of secure documents. In addition, the credential server 205 may manage authentication and authorization of users (e.g., users of the website 280 or users who make requests for usage through the server 220 may be authenticated by the credential server 205 using combinations of security information managed by the credential server 205, and, e.g., the credential server 205 may issue credentials to the client 220). For example, the credential server 205 may provide for specification of preferences (e.g., preferences for terms and conditions of a secure document) and relationships (e.g., relationships among users and users, organizations and users, organizations and users, and organizations and organizations), in addition to generation, distribution, and revocation of policies (e.g., policies for generation of a secure document or terms and conditions of a secure document) and digital credentials. For example, the secure document generation server 215 may retrieve necessary key information from the credential server 205 to package a secure container that may take the form of a secure electronic health record according to a specification that has been predefined with an insurance company for that specific insurance group. For example, different states or different companies may have different requirements for providing access or use of content to data content recipients, necessitating that generation of secure documents to be used as secure electronic health records may need to differ depending on the location of the data content subject's primary residence or the place where a data content recipient (e.g., a physician) is providing care such that content of a secure electronic health record is required. For example, policy preferences, such as a duration or location of access, may be part of terms and conditions of usage of information that are provided by the credential server 205.

The credential server 205 may use a relationship repository 225 to store information about individuals, organizations, and relationships, in addition to information about those individuals, organizations, and relationships. For example, a relationship between an insured party and an insurance company may be stored with preferences for access and usage of patient information of the insured party by the insurance company. For example, a relationship between a patient and a research institution may indicate that the research institution may view some types of medical information but not others (e.g., some types of secure holdings but not others). The relationship repository 225 may be implemented as a hierarchical or relational directory, identity management repository, or custom repository or product where individual and organization references are associated with credentials for access to resources and other attributes.

Attributes may include types of access and usage rights for a relationship (e.g., view, print, copy, modify, and the like), access and usage conditions (e.g., restricting viewing by Internet Protocol address, a geography defined by an Internet Protocol address, a time period (e.g., authorization may be valid for ninety days), and the like), types of authorized information (e.g., in a health care environment claims information may be authorized for view by an insurance company but not a research institution), roles (e.g., in a health care environment, a data content recipient having a doctor role may have different access and usage rights than a data content recipient being a hospital administrator), or some combination of the above or other attributes.

To determine whether access and usage rights are allowed for a relationship, information about a component of a secure document (e.g., information about a secure holding) may be used to classify the component such that it may be compared against attributes (e.g., metadata of a secure holding may indicate the holding includes claims information and an attribute of a relationship may indicate access and usage of the claims information is allowed).

In alternative implementations, access and usage rights need not be based on relationships between parties. For example, data content recipients may be associated with information that has access and usage rights attributes. In general, preferences for access of information may be based on a component level (e.g., in the structure 300 of FIG. 3, on the granularity of a secure holding, such as a classification of secure holdings).

Although relationships are discussed as being principal to principal relationships, relationships between parties may be based on profiles, stored as preferences of a principal in relationship repository 225, or using other techniques, mechanisms, or both. As another example, default preferences of a data content subject or the preferences of their relationships may also be used to determine outcomes for authorization. For example, a patient need not have an expressed relationship regarding an ability to provide access to treatment eligibility information, but a relationship between a patient's employer and the patient's current insurance company may have specified a setting for the patient's authorization of this information by default.

In scenarios involving a denial of access by the credential server 205, the credential server 205 may process a request for authorization (e.g., from a data content subject or data content custodian). Such a request may be forwarded to a data content subject or data content custodian, such that authorization may be permitted by user interaction. For example, a text message stating that a doctor is requesting access to a certain type of medical data may request a response for authorization being yes or no. Additional policies may be generated in response to such a request or may be considered a one-time exception to typical authorization processing. For example, a new relationship may be generated at the relationship repository 225 and that relationship may include attributes authorizing the data content recipient.

In general, secure documents of the repository 230 are secured to prevent access and use of their information. For example, each component of the secure document may be encrypted using an encryption scheme and the client 210 might not have a decryption engine, resources, or necessary credentials to decrypt the documents. To access the information of the documents, as described above, the server 220 may replace security of the documents with a security that can be removed by the client 210 (e.g., as a form of granting access). In some implementations, multiple clients may share a same authentication and security tool of the server 220. For example, multiple clients may request access to a component of a secure document from the server 220, each client 210 receiving access to that component using a negotiated second security that is different from the first security, but unique to itself, such that information may be accessed. Separate credentials presented by client 210 to server 220 on behalf of a specific user of client 210 may be used as criteria by which a negotiated second security that allows access to information of a secure document may be obtained.

The server 220 may maintain a log of events in the log repository 250. Different events may be logged. For example, the log may include an entry for each access, or attempted access, to a document by a client. Logged events may include varying granularities of detail. To ensure security of a log, the log may be encrypted, not include information that may easily be used to identify a person or company of which information is logged, or a combination of techniques and mechanisms may be implemented.

A log may be used to monitor access to and use of secure documents, parts of secure documents, or components of those parts that may assist ensuring security. For example, a data content subject may review log access to information distributed in secure documents to be assured that unauthorized users have not accessed that information. In a health care environment, some users may be required to monitor medical information and a log may be used as a compliance verification tool to determine if someone is monitoring information. Logging may include both accesses that are approved and denied. In some implementations, logging of approvals may include limited information whereas denials may include detailed information (e.g., to assist in showing a policy prevented access to information). For example, an entry of an approval may include metadata about information approved and a data content recipient, whereas a denial may further include a description of a policy of a user (e.g., a policy of a relationship of a data content subject and data content recipient) that led to a denial. The log may be viewed by, as examples, a user of the website 280 (e.g., to data content subjects, data content recipients, data content custodians, and the like) or a system administrator of the server 220. Authorization to view the log may be provided based on attributes associated relationships in the relationship repository 225 (e.g., and governed by the credential server 205).

Logging may include details of user operations other than access with respect to client 210 and server 220. For example, changes to access rights, such as an addition of a relationship, may be logged. As another example, system downtime may be logged. Logging may include details of allowed or denied operations that relate to actors other than the client 210 and the server 220. Access to log may also be controlled by a user authorization. Access to individual components of log information may be controlled by user authorization or attributes associated with a principal.

Contents or changes to a log may be distributed, or accessed as part of a secure or otherwise distributed communication to authorized parties that may have interest or requirements to observe the log and its changes. For example, a log may be distributed across different portions of one or more computer systems. As another example, updates about access to a patient's medical history may be communicated to the patient in the form of a secure document, an electronic mail notification, a text message, and the like. Similarly, for example, access to a patient's treatment eligibility or coverage information may be communicated to that patient's insurance company or payer, such that the organization may be notified of a potential opportunity to investigate an incident that may be of interest.

Although the system 200 of FIG. 2 includes a certain number and type of components, implementations may differ. For example, a number of clients, secure document generation servers, and servers may exist. As another example, a suite of services, application programming interfaces, or interfaces that include the operation of the web services 204, website 280, or a combination of components of the system 200 may be offered as a commercial service or product.

As another example, the client 210 may have credentials in addition to user credentials by which the server may establish trust of the client 210 (e.g., code signing of the client), such that the server 220 is able to verify that the client 210 adheres to established standards for governing user access and usage to data by the articulated authorization policy granted by the server 220.

As another example, an interface for providing access or usage of data to a user need not be a website, such as the website 280 and the interface of the client 210 may differ. For example, a suite of web-accessible services, such as services that might be accessed via SMS (Short Message Service), MMS (Multimedia Messaging Service), or IVR (Interactive Voice Response) system may be provided. The services may be exposed by an underlying application programming interface that may communicate with the secure document generation server 215, the credential server 205, and the server 220. The client 210, as examples, may be a mobile phone that accepts and composes text messages, a telephone, personal data assistant, and the like.

As another example, the hosting and granularity of features may differ. For example, the server 220, the website 280, and the credential server 205 may be hosted at a same site, different sites, or some combination of hosting may be performed. Similarly, the hosting of repositories need not be paired with servers and intermediate components may exist. For example, the relationship repository 225 need not be paired with the credential server 205 and a server may be used to interface with the relationship repository 225.

As another example, although the information repository 235 appears paired with the secure document generation server 215, that need not be the case. For example, the information repository 235 may reside on one or more servers remote from the secure document generation server 215. Also, the secure document generation server 215 need not contact the information repository 235 directly to receive information. For example, a component may act as a data broker, and the data broker may include a tool that facilitates synchronous or asynchronous ETML (Extraction, Transformation, Move, and Load of data e.g., data need not be available when requested); or data-level, process-level, or service-level integration between the secure document generation server 215 and the information repository 235 where the data broker allows for aggregation and integration of information remote from the secure document generation server 215.

The secure document generation server 215 need not provide information in a specific format. Information to supplement the generation of a secure document may be stored independently of a secure document. For example, metadata about a secure document may be collected and used independently of the secure document from which it is derived.

Although FIG. 2 includes a separation between a client 210 and a server 220, such a division need not exist. In general, the terms client and server may refer to client and server application programs, although, they may refer to client and server computer systems. A client and server are generally remote from each other and typically interact through a communication network; however, a client and server need not have a dedicated connection. The relationship of client and server may arise by virtue of one computer program, referred to as a server, providing a service to another computer program, referred to as a client. The server 220 may be referred to as a "clearing server," and a combination of the credential server 205 and the server 220 may be referred to as a "policy server," "identity management tool," or "policy management tool."

FIG. 3 is a diagram of a structure 300 for a secure document. The structure 300 may be referred to as a secure container and includes the secure holdings 310, metadata 320, and a rights management specification 330. The structure 300 may be a structure of the secure documents of the repository 230 of system 200 of FIG. 2. For example, one of the secure documents of the repository 230 of FIG. 2 may include one of the secure holdings 310 or portions of the secure holdings 310. For example, in a health care environment the structure 300 may be a secure electronic health record of a data subject and each of the secure holdings 310 may be portions of a health record, such as a set of test results, an x-ray image, and the like.

The secure holdings 310 are components of the structure 300 and each of them may be secure from access. For example, each of the secure holdings 310 may be encrypted. Each of the secure holdings 310 may have separate types of security or require separate credentials; a uniform type of security may be applied to the secure holdings 310; or some commonality of security may exist. For example, in health care environment, claims may be secured using a same protocol for their secure holdings while a different security protocol may be used for secure holdings of medical results, such as x-rays. In some implementations, the secure holdings 310 may include other information. For example, terms and conditions of use of content of the secure holdings 310 may be encrypted with each of the secure holdings 310. For example, terms and conditions may include a specification requiring the use of a specific issuing root public key certificate that is trusted to facilitate clearing of the content. Each of the secure holdings 310 may further include a unique identifier that allows the secure holdings 310 to be tracked, along with the structure 300 that was used at the time the structure 300 was constructed.

The metadata 320 may include information about the structure 300 and the secure holdings. In particular, the metadata 320 may include an index of the secure holdings 310 in the structure 300 and a general description of the structure 300. For example, in a health care environment, the metadata 320 may include non-sensitive biographical information about a patient and short descriptions of secure holdings 310 that may be searched on the basis of non-sensitive diagnosis and procedure codes. For example, information identifying a data content subject in one of the systems 100, 200 of FIGS. 1, 2 may be included without identifying an individual outside of the system (e.g., an identifier of a patient used in the systems 100, 200 but not related to a social security number), and that information may be used to identify the data content subject when determining whether a data content recipient is authorized to view secure holdings.

The rights management specification 330 may include a specification of data from a secure document generation server, such as the secure document generation server 215, that details security for the secure holdings 310. For example, in the health care environment, information about the building of a secure electronic health record may be included. In addition, information for a client to access the secure holdings may be included in the rights management specification 330. For example, information identifying a location of a server for providing authorization, which may be referred to as a clearing server, and a specification of roles and credentials that are eligible for requesting content access. The rights management specification 330 may be articulated in a declarative format (e.g., RFC 822 compliant file, eXtensible Markup Language dialect, runtime compiled scripting language, and the like) or programmatic format (e.g., application programming interface, and the like) used by a programmatic subsystem that encrypts data to generate a secure container.

Although the structure of FIG. 3 includes a certain number and type of features, additional, fewer, or different features may be included. For example, the rights management specification 330 may be combined with the metadata 320.

As another example, although FIG. 3 shows a first level of nesting of secure holdings 310 of the structure 300, there may be any number of levels of nesting of sub-components or sub-holdings. For example, a secure holding may have multiple secure sub-holdings. The secure sub-holdings themselves may be documents that are separately encrypted or an entire secure holding of a secure document may be encrypted. The security applied to sub-holdings may either be dependent or independent of the security applied to the secure holding of which it is apart. Similarly, different terms and conditions may be applied to different secure sub-holdings of the secure holding of a secure document. For example, in the generation of a secure document to reflect population-specific information, content for multiple data content subjects may be organized into individual sub-holdings of a parent secure holding that represents a specific classification of population information (e.g., diagnosis or disease identification information) while each secure sub-holding is independently governed by access and usage policies appropriate for each respective data content subject.

Although the structure of FIG. 3 includes a certain number and type of features, additional, fewer, or different features may be included. For example, the rights management specification 330 may be combined with the metadata 320.

FIG. 4 is a diagram of a structure of a table 400 of relationships and associated attributes. The table 400 may be part of the relationship repository 125 FIG. 1 or the relationship repository 225 of FIG. 2. In general, the table 400 includes headings 405 describing columns of the table 400 and table entries 410-450.

For each of the entries 410-450, a pair of first and second party identification is used to describe a relationship between the first and second party, where the first party may represent a parent node and the second party may represent a child node of the parent node in a graph of relationships (e.g., a directed graph). For example, the first entry 410 includes a first party John Smith and a second party Research Institution for Cancer, where John Smith may be considered the parent of Research Institution for Cancer.

The parties included in the first and second party columns 455 may include users and organizations, such that a combination of the columns may represent user to user, user to organization, organization to user, and organization to organization relationships. Attributes of relationships may be included in columns 460 associated with a relationship. For example, attributes of a row are associated with a relationship in that row defined by the first and second party columns 455. For example, a second entry 410 describes that a relationship between John Smith and Los Angeles Hospital is associated with authorization to view biographical information.

The attributes of relationships in the table 400 include access rights associated with a relationship and a temporal attribute of a relationship. For example, some of the attributes in columns 460 describe types of access allowed for a child of a parent, for a type of content in each of the columns 460. For example, a first attribute 465 of a fourth entry 410 describes that Doctor Simpson may only view and print biographical information of John Smith. As an example of a temporal attribute, the temporal attribute 470 that the relationship between OK Employers (e.g., a name of a company) and John Smith lasted from Jan. 1, 2006 to Jan. 1, 2007. A combination of attributes of a relationship may be referred to as a policy for a relationship.

The relationships specified in the table 400 may be used to determine indirect relationships among parties. For example, the relationship between John Smith and Los Angeles Hospital in the second entry 415 may indicate that Los Angeles Hospital has access rights to John Smith's records, the relationship between Los Angeles Hospital and Doctor Simpson may indicate that Doctor Simpson inherits the access rights of Los Angeles Hospital. In combination, the relationships may indicate that Doctor Simpson may access records of John Smith by virtue of the relationships with Los Angeles Hospital.

Different techniques may be used to resolve conflicts among relationships and identify attributes that should be used. For example, explicit, direct relationships may override implicit, indirect relationships. For example, the indirect relationship of Doctor Simpson and John Smith by virtue of their relationships with Los Angeles Hospital may be overridden by the explicit, direct relationship Between John Smith and Doctor Simpson in the fourth entry 425. Consequently, the attributes of the fourth entry 425 may be used for their relationship. In some implementations, to ensure a greater availability of information, attributes having less-restrictive access rights may override more restrictive access rights. In some implementations, a special scenario, such as emergency care in the health care environment, may override attributes of a relationship.

Relationships, their attributes, or both may be managed by a data content subject, data custodian, system administrator, and the like. For example, a user may desire that they do not wish to be affiliated with a hospital and may change attributes to revoke access or usage of their patient information from employees of the hospital. As another example, a relationship between an employer and employee may be generated by a system administrator and the request of an employer.

The table 400 illustrates how a user or organization may have relationships that reflect having multiple parents. For example, two entries 445, 450 include relationships between employers and John Smith, indicating different employers for different periods of time, according to the temporal attribute 470, where each of the employers, OK Employers and Best Employers are considered parents. Thus, a "many to many" cardinality of party relationships may exist, and some may include temporal distinctions.

Relationships that may be considered static or dynamic may be stored in the table 400. For example, organization to user and organization to organization relationships may be considered static, and user to organization or user to user relationships may be considered dynamic. For example, relationships that are considered static may include an insurance company and insured party, as such a relationship is not believed to change often. As another example, relationships between data content subjects and data content recipients may be considered dynamic as a data content subject may change such a relationship often.

While some relationships of the table 400 may indicate a data content recipient's access rights inherited from another party (e.g., from a data content subject or data content custodian), other types of relationships may be reflected. For example, where null attributes (e.g., no value or a zero value) are included for access rights, such as a fifth entry 430 between California Insurance and John Smith, the null attributes may indicate that relationships of the first party, or parent, may be used to find a relationship to the second party, or child. For example, the relationship of the fifth entry 430 may indicate that John Smith has all the relationships of California Insurance. For example, if John Smith does not otherwise have a relationship with a hospital named San Diego Hospital but California Insurance does, the access rights of that relationship may be used to determine access rights for content of John Smith to San Diego Hospital.

Although FIG. 4 uses the table 400 to define relationships and related attributes, other types of data structures may be used. In some implementations, another data structure, such as another table, may be used in addition to the table 400 of FIG. 4 to define relationships or attributes of a user or organization. For example, another table may define attributes of users or organizations. For example, secure containers associated with a data content subject, whether an organization or user may be available in another table and the relationships of table 400 may be used to determine whether a data content recipient has access rights to content about the data content subject. For example, in an environment using the secure container structure of FIG. 3, a user may have an attribute for each secure holding and each attribute may include a unique identifier of such a holding, and the unique identifier may be used by a secure document generation server, such as the secure document generation server 215 of FIG. 2, to generate a secure holding which may be downloaded.

Although table 400 includes a certain type and organization of information, implementations may vary. For example, fewer, additional or different attributes may be associated with a relationship. For example, attributes may further include a geography or Internet Protocol address for restricting content associated with a relationship (e.g., only doctors within a city may have access and usage of content of a certain patient; or, only computers accessing or using data within an Internet Protocol domain of a hospital may access or use content).

In some implementations, attributes of a relationship may describe a nature of a relationship. And, a same combination of parties may have multiple entries, where entries have different types of relationships. Also, part of an association may be a child type code, reference identifier code, and reference identifier code type. In that example, the child type code may represent a type of child that the parent would consider this type of child to be in a traditional directory server's organization unit structure (e.g., in an employer to employee relationship). The reference identifier code and reference identifier code type may permit multiple identification codes for a given relationship. For example, an insurance company may have a parent-child relationship with an employer, whereby the relationship is captured by both an internal employer id that is used for claims remission and reimbursement and a federal tax identification number that is used for the purpose of maintaining contracts.

Figure 5:
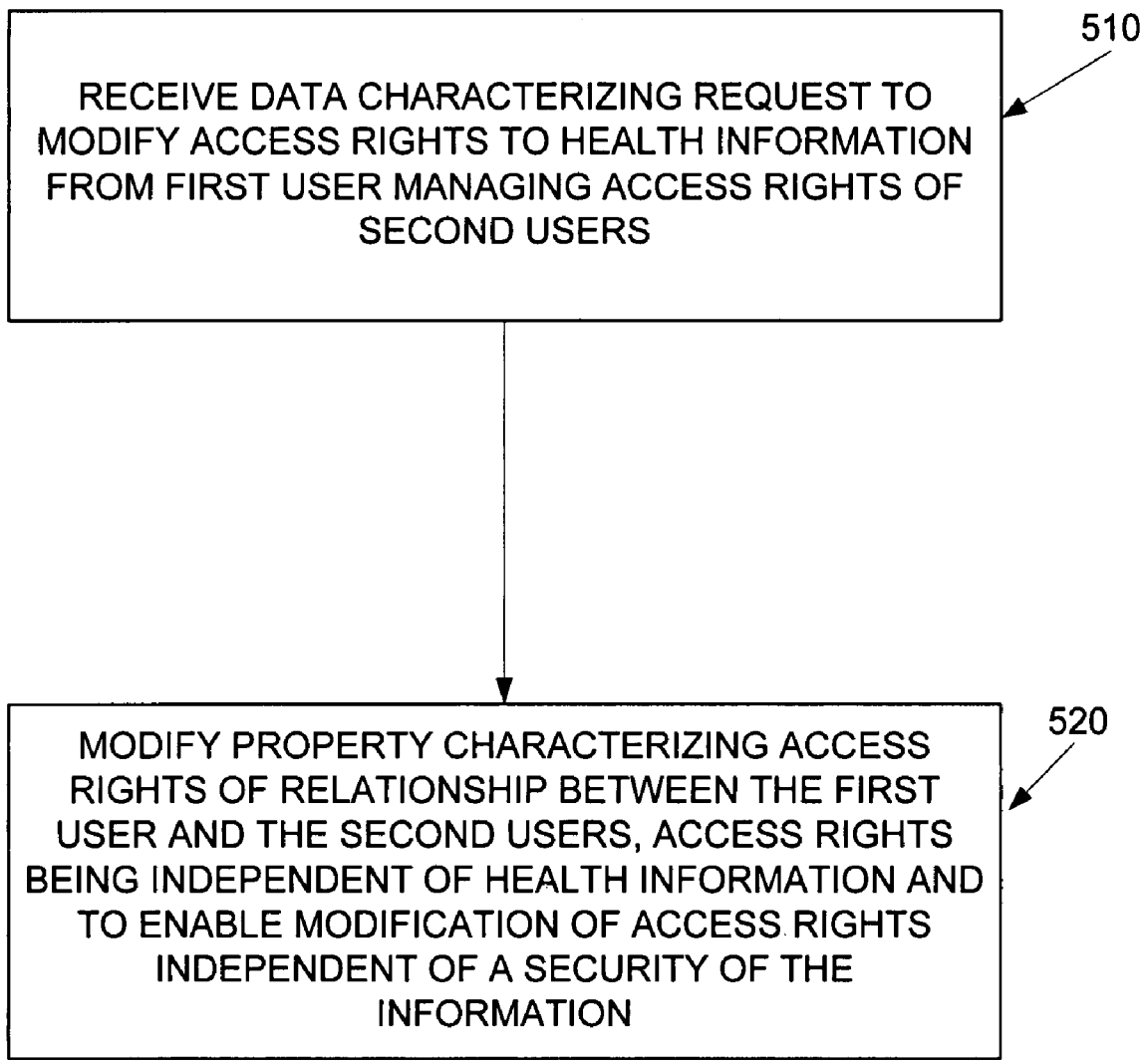
FIG. 5 is a flowchart illustrating a process of managing access or usage rights of content.

FIG. 5 is a flowchart illustrating a process 500 of managing access rights of health information. The process 500 may use the table 400 of FIG. 4, the structure 300 of FIG. 3, the system 100 of FIG. 1, the system 200 of FIG. 2, or a combination of those components. In general, the process 500 involves receiving a request to modify rights to access content, and modifying rights to access to content based on a relationship between a first user and one or more second users.

Although FIG. 5 refers to modification of access rights, access rights that are usage rights may be modified or conditions for usage may be modified. Similarly, although FIG. 5 refers to access rights of health information, access rights of other types of information or content may be modified.

Data characterizing a request to modify access rights to health information may be received from a first user managing access rights of second users (510). The data may be received at an interface to respond to such requests, such as website or web services, such as the website 180 or the web services 104 of FIG. 1. The data may be received at a server, such as a web server. The first user may be authenticated and authorized to manage rights of other users. For example, a data content subject may be authenticated and authorized to manage rights to access their health information. The data characterizing the request may, as examples, be a message or data received as input from user interaction. For example, the website 180 may send a message characterizing a request to modify access rights to the web services 104 of FIG. 1. The request may be generated by a user of a client or as part of a program. The request may include different types of information. For example, the request may include an indication of the first user and the second users, and a desired type of access to be granted to the second users.

A property characterizing access rights of a relationship between the first user and the second users, where the access rights are independent of health information and access rights are modified independent of a security of the information, may be modified (520). The property may be an attribute associated with a relationship between the first user and the second users. For example, the property may be one of the attributes in the columns of attributes 460 of FIG. 4. The access rights being independent of health information may include, as an example, the access rights being associated with the relationship in contrast to being associated with particular health information. For example, the attributes of the columns of attributes 460 of FIG. 4 are associated with a relationship rather than specific health information. Access rights being modified independent of a security of the information may include being able to modify access rights, such as revoking or granting access, without having to affect security of the health information. For example, in FIG. 2, the secure documents of the secure document repository 230 need not be encrypted in response to a change of access rights at the relationship repository 225. Modifying the property may include modifying one or more data structures that includes relationships managed by a server, such as the relationship repository 225 which is managed by the credential server 205.

Although FIG. 5 has a certain combination of sub-processes in a certain order, additional, fewer, or different sub-processes may be used and the order may differ. For example, the process 500 may be adapted for modifying access rights of a relationship between the first user and an organization of the second users. For example, the sub-process of 520 may include modifying a property characterizing access rights associated with a relationship between the first user and an organization of the second users. For example, a first user may have a relationship with a hospital and access rights associated with that relationship may be modified while access rights of a relationship between the hospital and its doctors need not change.

In addition to process 500, other sub-processes may be performed. For example, the first user may be authenticated, authorized, or both before modifying access rights. For example, the first user may send credentials, and the credentials may be used to determine whether the first user is authenticated and authorized to modify access rights.

As another example, requests for access to health information may be serviced. For example, data characterizing a request for access to health information may be received. The data may be received at a server to respond to requests for access to health information, such as the server 220 of FIG. 2. The request may have been generated by a client attempting to access secure health information, such as the client 210 of FIG. 2 that requests secure documents that may include secure health information. The data characterizing the request may be a message including secure health information and metadata for the secure health information. For example, a secure holding of a medical record may be sent with an identifier of a data content subject. The request may be generated by a user of a client or as part of a program. For example, a request may be generated when a program attempts to access secure health information as part of performing a task that uses the health information. The request may include a type of access requested.

Then, a determination may be made as to whether a requesting user is authenticated, authorized, or both for access to health information based on relationships of a requesting user. For example, the request may be based on explicit or implicit relationships of a requesting user (e.g., to the first user modifying access rights). The determination may involve determining whether a requesting user has an explicit relationships with a user or organization from which access may be granted. For example, determining whether the table 400 of FIG. 4 includes a relationship between a requesting user and a data content subject (e.g., of the content being requested). As another example, the determination may include determining whether a relationship between a requesting user and a data content subject may be implied from a combination of multiple relationships. For example, a combination of a relationship of a hospital to a doctor, where the doctor is a requesting user, and a relationship of a data content subject and the hospital may be combined to imply a relationship between the data content subject and the doctor. In addition, the determination may involve determining which types of access are authorized. And, if a requesting user is authenticated, authorized, or both (depending on the implementation), access may be enabled to be performed. For example, a version of health information with security replaced or removed may be sent to a requesting user with a list of access rights to be enforced at a client, such as the client 210 of FIG. 2.

For example, first credentials may be used to identify an account of a data content recipient. Metadata of secure health information that is sent with a request to access the health information may be used to determine an account of the data content subject. Then, a table of relationships may be queried to determine if the data content subject and data content recipient have a direct or indirect relationship. If a relationship does not exist, the data content recipient might not be granted access. If a relationship does exist, the relationship may include access right preferences that may be used to determine access rights to grant to a data content recipient. In addition to removing security in accordance with second security credentials, other types of security may be added. For example, the server 220 of FIG. 2 may decrypt a document using a private key and then encrypt the document using a session key negotiated for a secure server session.

Other information about a user may be used to determine access rights. For example, a data content recipient may be associated with one or more roles, such as doctor role, administrator role, and the like, which may define a granularity of access rights for an organization. For example, for a data content subject having a relationship with a hospital, doctors having a doctor role may have more access rights than administrative staff having an administrative role.

Although FIGS. 1-5 are discussed with references to examples in a health care environment, similar techniques and mechanisms may be employed in other environments.

A user, as discussed with reference to FIGS. 1-5 generally refers to a person who manipulates an input device to interact with a computer; however, the term user need not be so limited. For example, a user may be a computer program that acts as a user. For example, the client 210 of FIG. 2 may be used by a program and such a client may include, for example, an application programming interface in lieu of a graphical user interface.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, i.e., one or more computer programs tangibly embodied in an information carrier, e.g., in a machine-readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other in a logical sense and typically interact through a communication network. The relationship of client and server arises by virtue of computer programs running on the respective computers and having a client-server relationship to each other.

The subject matter described herein has been described in terms of particular embodiments, but other embodiments can be implemented and are within the scope of the following claims. For example, operations can differ and still achieve desirable results. In certain implementations, multitasking and parallel processing may be preferable. Other embodiments are within the scope of the following claims

What is claimed is:

1. A tangible computer readable storage medium comprising computer executable instructions that are configured to, when executed, cause a data processing apparatus to perform operations comprising:
   receiving data characterizing a request to modify access and usage rights of health information of a subject, the health information being secured by a security, the request being from a first user managing the access and usage rights of a second one or more other users to the health information;
   determining to what extent the first user is permitted to modify the access and usage rights of the second one or more other users as a function of a relationship between the first user and the health information, wherein a table of relationships is queried to determine if the first user has at least an indirect relationship to the subject;
   maintaining a data store including a plurality of data structures, each of the data structures corresponding to a relationship type, and each of the data structures including information describing the access and usage rights, wherein the data store is further configured to store policy preferences related to the access and usage rights, and wherein the information describing the access and usage rights relates to the relationship type; and
   modifying the access and usage rights in accordance with the request, the modifying comprising:
      modifying a property characterizing the access and usage rights of a relationship between the first user and the second users, the relationship being stored in at least one of the plurality of data structures, the access and usage rights being independent of the health information in order to enable modification of the access and usage rights independent of the security of the health information such that the security of the health information need not be changed in response to the modification of the property.

2. The computer program product of claim 1, wherein the access and usage rights comprise one or more of rights for viewing, copying, printing, or exporting the health information.

3. The computer program product of claim 1, wherein the receiving and the modifying are performed by services that may interface with a user interface.

4. The computer program product of claim 3, wherein the user interface is a website.

5. The computer program product of claim 1, wherein the health information is a secure electronic health record.

6. The computer program product of claim 1, wherein the health information is a secure holding of a secure electronic health record.

7. The computer program product of claim 6, wherein security of the secure holding differs from security of one or more other secure holdings of the secure electronic health record.

8. The computer program product of claim 6, wherein access rights of the secure holding differ from access rights of one or more other secure holdings of the secure electronic health record.

9. The computer program product of claim 1 further comprising:
   storing the modified property.

10. The computer program product of claim 1 further comprising:
   receiving a request from the second users to access or use the health information at a first time later or earlier than a second time of another request, the request being approved or denied based on the modifying the property to approve or revoke access.

11. The computer program product of claim 1, wherein the operations of the receiving and the modifying are performed at a server and the operations further comprise requesting from a client of at least one of the second users access of the health information and the server determining whether to grant access depending on the property characterizing the access and usage rights of the relationship between the first user and the second users.

12. The computer program product of claim 1, wherein the relationship types include user to user relationships, organization to user relationships, user to organization relationships, and organization to organization relationships, the relationships of the plurality of data structures associated with one or more attributes of access and usage rights between parties of at least some of the relationships, a combination of relationships used to determine indirect relationships, and the relationships describing a graph of relationships of the parties.

13. A computer-implemented method for use with a data store containing a plurality of data structures, the method comprising:
   receiving data characterizing a request to modify access and usage rights of health information of a subject, the health information being secured by a security, the request being from a first user managing the access and usage rights of a second one or more other users to the health information;
   determining to what extent the first user is permitted to modify the access and usage rights of the one or more other users as a function of a relationship between the first user and the health information, wherein a table of relationships is queried to determine if the first user has at least an indirect relationship to the subject;
   maintaining the data store including the plurality of data structures, each of the data structures corresponding to a relationship type, and each of the data structures including information describing the access and usage rights, wherein the data store is further configured to store policy preferences related to the access and usage rights, and wherein the information describing the access and usage rights relates to the relationship type; and modifying the access and usage rights in accordance with the request, the modifying comprising:

modifying a property characterizing the access and usage rights of a relationship between the first user and the second users, the relationship being stored in at least one of the plurality of data structures, the access rights being independent of the health information in order to enable modification of the access and usage rights independent of the security of the health information such that the security of the health information need not be changed in response to the modification of the property.

14. The method of claim 13, wherein the receiving and the modifying are performed by services that may interface with a user interface.

15. The method of claim 13, wherein the health information is a secure holding of a secure electronic health record.

16. The method of claim 13, wherein the operations of the receiving and the modifying are performed at a server and the operations further comprise requesting from a client of at least one of the second users access and usage of the health information and the server determining whether to grant access depending on the property characterizing the access and usage rights of the relationship between the first user and the second users.

17. A tangible computer readable storage medium comprising computer executable instructions that are configured to, when executed, cause a data processing apparatus to perform operations comprising:

receiving data characterizing a request to modify access and usage rights of health information of a subject, the health information being secured by a security, the request being from a first user managing the access and usage rights of a second one or more other users to the health information;

determining to what extent the first user is permitted to modify the access and usage rights of the second one or more other users as a function of a relationship between the first user and the health information, wherein a table of relationships is queried to determine if the first user has at least an indirect relationship to the subject;

maintaining a data store including a plurality of data structures, each of the data structures corresponding to a relationship type, and each of the data structures including information describing access and usage rights, wherein the data store is further configured to store policy preferences related to the access and usage rights, and wherein the information describing the access and usage rights relates to the relationship type; and modifying the access and usage rights in accordance with the request, the modifying comprising:

modifying a property characterizing the access and usage rights of a relationship between the first user and an organization comprising the second users, the relationship being stored in at least one of the plurality of data structures, the access and usage rights being independent of the health information in order to enable modification of the access and usage rights independent of the security of the health information such that the security of the health information need not be changed in response to the modification of the property.

18. The computer program product of claim 17, wherein the receiving and the modifying are performed by services that may interface with a user interface.

19. The computer program product of claim 17, wherein the operations of the receiving and the modifying are performed at a server and the operations further comprise requesting from a client of at least one of the second users access and usage of the health information and the server determining whether to grant access depending on the property characterizing the access and usage rights of the relationship between the first user and the organization of the second users.

* * * * *